United States Patent [19]

Henry et al.

[11] 3,954,766

[45] May 4, 1976

[54] 1,4-DIAZABICYCLO[3.2.1]OCTANES

[75] Inventors: David W. Henry, Menlo Park; Priscilla A. Sturm, Mountain View, both of Calif.

[73] Assignee: Stanford Research Institute, Menlo Park, Calif.

[22] Filed: July 9, 1975

[21] Appl. No.: 594,510

[52] U.S. Cl. ............................ 260/268 BF; 424/250
[51] Int. Cl.² ...................................... C07D 487/08
[58] Field of Search .............................. 260/268 BF

[56] References Cited

UNITED STATES PATENTS 3,905,979   9/1975   Henry et al. ................... 260/268 BF

*Primary Examiner*—Alton D. Rollins
*Assistant Examiner*—Jose Tovar
*Attorney, Agent, or Firm*—Donovan J. De Witt

[57] ABSTRACT

The compounds 4-carbethoxy-1,4-diazabicyclo[3.2.1]octane and 4-diethylcarbamyl-1,4-diazabicyclo[3.2.1]octane, said compounds having utility as antifilarial agents.

3 Claims, No Drawings

1,4-DIAZABICYCLO[3.2.1]OCTANES

ORIGIN OF INVENTION

The invention described herein was made in the course of work under a grant or award from the Department of Health, Education and Welfare.

SUMMARY OF INVENTION

The invention relates to the provision of the novel compounds 4-carbethoxy-1,4-diazabicyclo[3.2.1]octane having the structure

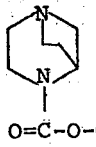

and 4-diethylcarbamyl-1,4-diazabicyclo[3.2.1]octane having the structure

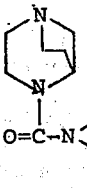

Also included in the invention are pharmaceutically acceptable salts of these compounds, the salts being acid addition salts and water soluble.

A method for preparing each of the foregoing compounds is presented in the following examples. In general, however, the preparation is one wherein 2-(2-hydroxyethyl)-pyrazine (L. J. Kitchen and E. S. Hanson, Antibiot. Chemo., 73, 1838 (1951)) was reduced with $H_2$ and $PtO_2$ in MeOH to yield 2-(2-hydroxyethyl)-piperazine (E. F. Rogers and H. J. Becker, U.S. Pat. No. 3,281,423 (1966)) which, in turn, was converted to the chloride. Ring closure in base afforded 1,4-diazabicyclo[3.2.1]octane which was acylated with ethylchloroformate to give 4-carbethoxy-1,4-diazabicyclo[3.2.1]octane or with diethylcarbamyl chloride to give 4-diethylcarbamyl-1,4-diazabicyclo[3.2.1]octane.

EXAMPLE 1

4-Carbethoxy-1,4-diazabicyclo[3.2.1]octane
2-(2-Hydroxyethyl)piperazine

A suspension of 30.0 g (0.242 mol) of 2-(2-hydroxyethyl)pyrazine (L. J. Kitchen and E. S. Hanson, Antibiot. Chemo., 73, 1838 (1951)) in 475 ml MeOH and 7.5 g 85% $PtO_2$ was hydrogenated in two equal portions on a Parr Shaker. The reaction became quite warm to touch after 5 min of shaking. The shaker was stopped to allow for cooling (15–20 min), and then shaking continued for 24 hr. Each reaction was filtered, combined with 1 g of fresh $ptO_2$ and the reaction was continued for another 24 hr. Filtration and evaporation yielded 30.0 g (95%) pale yellow oil. An earlier probe that behaved similarly had yielded a very hygroscopic HCl salt, mp 170°–200° (E. F. Rogers and H. J. Becker, U.S. Pat. No. 3,281,423 (1966) mp 210°) and a dipicrate, mp 237°–241°C from $H_2O$.

Analysis calculated for $C_6H_{14}N_2O.2C_6H_3N_3O_7.H_2O$ (percent): C, 35.7; H, 3.66; N, 18.5. Found (percent) C, 35.6; H, 3.69; N, 18.4.

2-(2-Chloroethyl)piperazine dihydrochloride (E. F. Rogers and H. J. Becker, U.S. Pat. No. 3,281,423 (1966).) To 25.0 g (0.192 mol) of 2-(2-hydroxyethyl)piperazine, chilled in dry ice, 125 ml $SOCl_2$ was cautiously added dropwise. After addition was complete, the mixture was cautiously heated on a steam bath with stirring for 2 hr. The reaction was cooled and treated cautiously with $H_2O$ until a solution resulted. The reaction was evaporated to dryness, and the dark residue was redissolved in $H_2O$ and filtered. The dark filtrate was heated on the steam bath with decolorizing carbon for 30 min and filtered to yield a pale yellow solution. Acetone was added to precipitate the product in two crops: 29.3 g white solid, mp 336°–339° dec., and 11.6 g (total 96% yield) pale-yellow solid, mp 330°–350° dec. (E. F. Rogers and H. J. Becker, U.S. Pat. No. 3,281,423 (1966) mp 348°–350° dec.)

1,4-Diazabicyclo[3.2.1]octane (E. F. Rogers and H. J. Becker, U.S. Pat. No. 3,281,423 (1966)). To a barely stirring suspension of 11.6 g 2-(2-chloroethyl)piperazine dihydrochloride (0.0523 mol) in 8.7 ml $H_2O$ was added a soln of 8.7 g (0.378 mol) NaOH in 8.7 ml $H_2O$, which effected almost complete solution. The resulting solution was extracted 3 times with $CHCl_3$; the combined extracts were dried with $Na_2SO_4$, filtered, and evaporated to give 5.68 g of yellow oil. This was treated with excess conc HCl and evaporated to dryness. The semisolid was triturated in acetone and EtOH, quickly filtered, and dried under $N_2$ to yield 6.75 g (70%) di.HCl salt, mp 340° dec. (E. F. Rogers and H. J. Becker, U.S. Pat. No. 3,281,423 (1966) mp 348° dec.).

Analysis calculated for $C_6H_{12}N_2.2HCl$ (percent): C, 38.9; H, 7.62; N, 15.1. Found (percent): C, 38.7; H, 7.54; N, 15.1.

4-Carbethoxy-1,4-diazabicyclo[3.2.1]octane

To 2.0 g (0.0108 mol) of 1,4-diazabicyclo[3.2.1]octane.2HCl and 1.73 g NaOH (0.0432 mol) in 20 ml $H_2O$ was added 20 ml $CHCl_3$. After stirring briefly at 0°, ethyl chloroformate, 1.76 g (1.56 ml, 0.0162 mol) was added and the reaction was stirred for 2 hr at room temperature. The two phases were separated, and the aqueous phase was extracted twice with $CHCl_3$. The combined extracts were dried with $Na_2SO_4$, filtered, and evaporated to yield 620 mg crude oil. A soln of this in EtOH was treated with conc HCl and evaporated to dryness. The hygroscopic product was isolated from EtOH:$Et_2O$ (1:20) by centrifuging and drying under $N_2$ to yield 524 mg white solid, mp 173°–177°, after drying.

Analysis calculated for $C_9H_{16}N_2O_2.HCl$ (percent): C, 49.0; H, 7.76; N, 12.7. Found (percent): C, 48.8; H, 7.88; N, 12.7.

Retreatment of the aqueous phase with ethyl chloroformate gave an additional 226 mg of 4-carbethoxy-1,4-diazabicyclo[3.2.1]octane.HCl (mp 179°–182°, 31% yield).

EXAMPLE 2

4-Diethylcarbamyl-1,4-diazabicyclo[3.2.1]octane

To 1.0 g (0.00542 mol) 1,4-diazabicyclo[3.2.1]octane.2HCl and 2.4 ml (1.75 g = 0.0173 mol) triethylamine in 4 ml dioxane was added 0.735 g (0.542 mol) diethylcarbamyl chloride. The solution was stirred overnight at room temperature. $Et_2O$ was added to precipitate fully $Et_3N.HCl$, which was collected by filtration and washed with $Et_2O$. The filtrate was evaporated to dryness, and $H_2O$ was added to azeotrope off the dioxane. The residue was treated with conc HCl and partitioned between $H_2O$ and $CHCl_3$. The $H_2O$ layer was evaporated to dryness, and the residue was triturated in $Et_2O.EtOH$. The insoluble product was collected by centrifugation and dried under $N_2$. Yield: 582 mg (43%) white solid, mp 195°–203°.

Analysis calculated for $C_{11}H_{21}N_3O.HCl$ (percent): C, 53.3; H, 8.95; N, 17.0. Found (percent) C, 53.2; H, 8.80; N, 17.0.

For generic purposes the compounds of the present invention may be said to have the structure

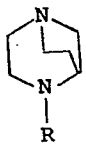

where R is a $-CO_2C_2H_5$ or $-CON(C_2H_5)_2$ radical.

When evaluated against Litomosoides carinii in the gerbil all the compounds hereof strongly suppressed blood microfilaremia levels but did not affect the adult worms. Several compounds were nearly equivalent to diethylcarbamazine in activity.

The compounds of the present invention have been described in the examples in the form of acid addition salts, such salts being water soluble and therefore of somewhat greater utility than the compounds would be without the inclusion of the acid component. In preparing the compounds as salts, any pharmaceutically acceptable acid material may be employed, e.g., hydrochloride acid, sulfuric acid, citric acid, or acetic acid, for example. The pure compounds can be prepared in non-salt form by treating the salt with alkali in aqueous solution, the compound being extracted from the aqueous reaction system with a solvent such as diethyl ether or chloroform. The evaporation of the solvent then leaves the non-salt compound.

What is claimed is:

1. A compound of the formula

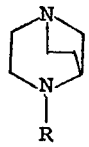

where R is a $-CO_2C_2H_5$ or $-CON(C_2H_5)_2$ radical, or the pharmaceutically acceptable acid addition salts thereof.

2. The compound of claim 1 which is 4-carbethoxy-1,4-diazabicyclo[3.2.1]octane, or the pharmaceutically acceptable acid addition salts thereof.

3. The compound of claim 1 which is 4-diethylcarbamyl-1,4-diazabicyclo[3.2.1]octane or the pharmaceutically acceptable acid addition salts thereof.

* * * * *